United States Patent [19]
Krier

[11] Patent Number: 6,156,957
[45] Date of Patent: *Dec. 5, 2000

[54] INBRED CORN LINE NP 991

[75] Inventor: Merl R. Krier, Northfield, Minn.

[73] Assignee: Novartis AG, Basel, Switzerland

[*] Notice: This patent issued on a continued prosecution application filed under 37 CFR 1.53(d), and is subject to the twenty year patent term provisions of 35 U.S.C. 154(a)(2).

[21] Appl. No.: 08/728,715

[22] Filed: Oct. 11, 1996

Related U.S. Application Data

[63] Continuation of application No. 08/567,612, Dec. 5, 1995.
[51] Int. Cl.[7] ............................... A01H 5/00; A01H 4/00; C12N 5/04
[52] U.S. Cl. ...................... 800/320.1; 800/298; 800/275; 800/271; 435/412; 435/424; 435/430; 435/430.1
[58] Field of Search ...................................... 800/200, 235, 800/250, DIG. 56, 320.1, 298, 275, 271; 435/240.1, 240.4, 240.47, 240.49, 240.5, 412, 424, 430, 430.1; 47/58, DIG. 1

[56] References Cited

U.S. PATENT DOCUMENTS 5,082,992  1/1992  Ambrose et al. ........................ 800/200

OTHER PUBLICATIONS

Coe et al. In Corn and Corn Improvement. Third Edition. Sprague et al., eds. Ch 3:81–137. ASA–CSSA–SSSA, Jan. 1988.

Hallauer et al. In Corn and Corn Improvement. Third Edition. Sprague et al. eds. Ch 8:463–564. ASA–CSSA–SSSA, Jan. 1988.

*Primary Examiner*—Gary Benzion
*Attorney, Agent, or Firm*—Lynn Marcus-Wyner

[57] ABSTRACT

An inbred corn line, designated NP 991, is disclosed. The invention relates to the seeds of inbred corn line NP 991, to the plants of inbred corn line NP 991 and to methods for producing a corn plant produced by crossing inbred line NP 991 with itself or with another corn plant. The invention further relates to hybrid corn seeds and plants produced by crossing inbred line NP 991 with another corn line.

11 Claims, No Drawings

INBRED CORN LINE NP 991

This is a continuation of application Ser. No. 08/567,612, filed on Dec. 5, 1995.

BACKGROUND OF THE INVENTION

This invention relates to a new and distinctive corn inbred line designated NP '991 and to hybrids made by using NP 991 as a parent.

Corn (*Zea mays*) is a valuable and important field crop. Thus, plant breeders are continually developing new and superior corn inbred lines for production of high yielding, agronomically sound hybrids. The goal of the plant breeder is to combine in a single variety or hybrid an improved combination of desirable traits from the parental germplasm. These traits may include maximized yield, resistance to disease and insects, tolerance to drought, heat and other environmental stresses.

Corn hybrid development requires the development of homozygous inbred lines, the crossing of these lines, and the subsequent evaluation of those crosses. Pedigree, backcross, and recurrent selection breeding methods are used to develop inbred lines from breeding populations. Breeding programs combine the genetic backgrounds from two or more inbred lines or various other genetic sources into breeding pools from which new inbred lines are developed by self pollination and selection of desired phenotypes. The new inbred lines are crossed with other inbred lines, and hybrids from these crosses are evaluated to determine which have commercial potential.

Once the inbred parents that give a superior hybrid are identified, the hybrid seed can be reproduced indefinitely as long as inbred parent homogeneity is maintained. Corn hybrids may be either single cross hybrids, produced when two inbred lines are crossed to produce the first generation ($F_1$) progeny; double cross hybrids, produced from four inbred lines crossed in pairs (A×B and C×D) and then the two $F_1$ hybrids are crossed again (A×B)×(C×D); or three-way cross hybrids produced from crossing a single cross (A×B) to a third inbred line C. Numerous references are available on the topic of corn breeding and hybrid seed corn production; those skilled in the art of corn breeding and production are well aware of techniques and methods for the development of inbred corn lines and corn hybrids. Reference is made particularly to Corn and Corn Improvement, Third Edition, eds. G. F. Sprague and J. W. Dudley, American Society of Agronomy Monograph No. 18, particularly chapters 8 and 9 the substantive content of which is hereby incorporated by reference.

SUMMARY OF THE INVENTION

According to the invention, there is provided a novel inbred corn line, designated NP 991. This invention thus relates to the seeds of Inbred corn line NP 991, to the plants of inbred corn line NP 991 and to methods of producing a corn plant comprising the crossing of inbred line NP 991 with itself or another corn line. This invention further relates to hybrid corn seeds and plants produced by crossing the inbred line NP 991 with another corn inbred line.

DEFINITIONS

In the description and examples that follow a number of terms are used; therefore, to provide a clear and consistent understanding of the specification and claims the following definitions are provided.

RK=Round Kernels: the percentage of kernels that do not pass through a 13/64 slotted screen.

HE=Husk Extension: the length (cm) of the husk past the ear tip at maturity.

PRM=Predicted Relative Maturity. This trait is based on the harvest moisture of the grain. The relative maturity rating is based on a known set of checks and is referred to as the Minnesota Relative Maturity Rating System.

MST=Harvest Moisture. The moisture is the actual percentage moisture of the grain at harvest.

STK (BR)=The percentage of plants broken below the ear at harvest.

YLD=Yield; bushels per acre. The actual yield of the grain at harvest (bu/a) adjusted to approximately 15.5% moisture.

RT=Percent of plants lodged (leaning from vertical but not broken).

PLT. HT.=Plant Height; The lenght of the plant to tassel tip (cm).

HU=Heat Units;

$$\frac{\text{Max Temp} (\leq 86° \text{ F.}) + \text{Min Temp} (\geq 50° \text{ F.})}{2} - 50$$

EAR HT.=Ear Height. The measure from the ground to the top developed ear node attachment measured in cm.

DETAILED DESCRIPTION OF THE INVENTION

Inbred corn line NP 991 is a yellow dent inbred line with superior characteristics and provides an excellent parental line in crosses for production of first generation $F_1$ corn hybrids. NP 991 is particularly suited as a female and is adapted to the North central part of the United States. NP 991 can be used to produce hybrids from approximately 85 to 100 days relative maturity based on the Minnesota Relative Maturity Rating System for harvest of grain. Inbred line NP 991 has demonstrated good combining ability with families derived from OH43 or Iodent type backgrounds.

Inbred corn line NP 991 was developed from the backcross population (H8431*1×L8401) by self-pollination and use of standard single pedigree ear-to-row breeding. H8431 is a Northrup King Co. proprietary line derived from other Northrup King Co. proprietary lines which are all derivatives of Iowa Stiff Stalk Synthetic. L8401 is a line derived from Pioneer Hybrid 3906 commercially available from Pioneer Hi-Bred International. Self-pollination and selection were practiced within the above $F_1$ cross for seven generations in the development of NP 991. During the development of the line, crosses of segregating families were made to inbred testers to evaluate general and specific combining ability. Inbred line NP 991 can be reproduced by planting seeds of the line, growing the resulting corn plants under self-pollination or sib-pollination conditions with adequate isolation and then harvesting the resulting seed. No particular variant traits have been observed or are expected in NP 991.

The inbred line has been evaluated at numerous research stations across the Northern United States Corn Belt and Canada. Inbred line NP 991 has shown uniformity and stability for all discernible characteristics as described in the following variety description (Table 1). The description is based on data collected primarily at Stanton, Minnesota and London, Ontario on a maximum of 9 replications. In interpreting the color designation herein, reference is made to the Munsell Glossy Book of Color, a standard color reference.

TABLE 1

VARIETY DESCRIPTION INFORMATION FOR INBRED LINE NP 991

|  | NP991 | CM105 |
|---|---|---|
| Type: | Dent | |
| Region Best Adapted: | North central | |
| A. Maturity: | | |
| HU to Silk (HUS): | 1226 (days 67) | 1220 (days 69) |
| HU to pollen : | 1195 (days 70) | 1195 (days 70) |
| B. Plant Characteristics: | | |
| Plant height (to tassel tip): | 205.7 cm | 187.2 cm |
| Length of top ear internode: | 15.8 cm | 12.8 cm |
| Ear height (to base of top ear internode): | 73.2 cm | 55.3 cm |
| Number of tillers: | none | none |
| Number of ears per stalk: | slight two-ear tendency | slight two-ear tendency |
| Cytoplasm type: | normal | normal |
| C. Leaf: | | |
| Color: | dark green (7.5GY-3/4) | dark green (7.5GY-4/2) |
| Angle from stalk (upper half): | 30–60 degrees | 30–60 degrees |
| Number of leaves (above top ear): | 5.3 | 5.3 |
| Marginal waves: | few | few |
| Width (widest point of ear node leaf): | 8.2 cm | 7.0 cm |
| Sheath Pubescence: | light (1.3) | light (3.0) |
| Longitudinal creases: | medium (4.5) | medium (4.3) |
| Length (ear node leaf): | 78.7 cm | 78.1 cm |
| D. Tassel: | | |
| Number of lateral branches: | 6.3 | 4.1 |
| Branch angle from central spike: | 15–30 degrees | 15–30 degrees |
| Pollen shed: | medium | medium |
| Anther color: | green-yellow | green-yellow |
| Glume color: | green-yellow | green-yellow |
| E. Ear (Husked ear data except where stated otherwise): | | |
| Length: | 13.6 cm | 13.8 cm |
| Weight: | 119.2 gm | 91.3 gm |
| Midpoint diameter: | 40 mm | 38 mm |
| Kernet rows: | 14 | 14 |
| Silk color: | purple | green-yellow |
| Husk extension: | medium (<8 cm) | medium (<8 cm) |
| Husk leaf: tightness | loose (2.5) | medium (6.0) |
| Taper of ear: | average | average |
| Position of shank (dry husks): | upright | upright |
| Husk color (fresh): | green-yellow | yellow |
| Husk color (dry): | tan | tan |
| Shank length: | 12.3 cm | 12.4 cm |
| F. Kernel (Dried): | | |
| Size (from ear mid-point): | | |
| Length (mm): | 11.4 | 10.3 |
| Width (mm): | 8.2 | 8.0 |
| Thickness (mm): | 4.2 | 7.2 |
| Shape grade (% rounds): | 10–20 | 10–20 |
| Aleurone color pattern: | homozyous | homozyous |
| Endosperm color: | yellow | yellow |
| Endosperm type: | normal starch | normal starch |
| Gm weight/100 seeds (unsized): | 24.8 | 15.8 |
| G. Cob: | | |
| Diameter at mid-point (cm): | 2.1 | 2.8 |
| Color: | red | red |
| H. Disease Resistance: | | |
| Northern Leaf Blight (Helminthosporium, R1&2): | Intermediate | |
| Eyespot (*Kabatielaa zeae*): | Resistant | |
| Grey Leaf Spot (*Cercospora zeae-maydis*): | Susceptible | |

The above disease resistance description is based on a scale of 1–9; 1–3 is considered susceptible, 4–5 intermediate, 6–7 resistant and 8–9 highly resistant.

Inbred corn line NP 991 most closely resembles public inbred variety Canada-Morden CM 105 is terms of usage and maturity and may be distinguished from Canada-Morden inbred CM105 by the characteristics summarized in Table 1 above.

This invention is also directed to methods for producing a corn plant by crossing a first parent corn plant with a second parent corn plant, wherein the first or second corn plant is a corn plant of the inbred line NP 991. However, both first and second parent corn plant can come from the inbred corn line NP 991. Therefore any methods using NP 991 are part of this invention including self-pollination, backcross-pollination, hybrid breeding and crosses to populations. It may be desirable to use a male-sterile (either cytoplasmic or nuclear) female parent to prevent self-pollination. If the female is not male-sterile, then either physical or chemical steps should be taken to ensure that self-pollination does not occur. Any plants produced using inbred corn line NP 991 as a parent are within the scope of this invention including any plant produced by the use of cells, protoplasts or tissue from NP 991. Advantageously, the inbred line NP 991 is used in crosses with other corn varieties to product first generating ($F_1$) corn hybrid seed and plants with superior characteristics.

Specifically NP 991 produces hybrids that are competitive yielding and have improved root strength particularly under high plant populations. Additionally, hybrids produced have good stalk quality. The techniques used to obtain the corn hybrid seeds and plants are conventional in the seed industry and are well known to those skilled in the art. The two parent varieties were planted in pollinating proximity to each other in alternating sets of rows; however, any convenient planting pattern that allows for the free transfer of pollen is acceptable. The plants of both inbred lines are allowed to grow until the time of flowering. At flowering, tassels are removed from all plants of the female parent by hand, machine or other means. Natural cross-pollination is allowed to occur. When NP 991 is a female parent, ears from the female plants are harvested to obtain novel $F_1$ hybrid corn seeds of the present invention. $F_1$ hybrid corn plants of the invention are obtained by planting seeds of the hybrid corn plant.

The data in Table 2 shows the relative hybrid performance of corn inbred line NP 991 crossed to Northrup King Co. proprietary inbred line NP 904, hereinafter NP 991×NP 904, compared to Northrup King Co. proprietary inbred line NP 904 crossed to Northrup King Co. proprietary line NP 807, hereinafter NP 904 X NP 807. Corn hybrid NP 904 X NP 807 is a proprietary hybrid currently being sold in the northern United States. Inbred line NP 904 has PVP Certificate No. 9200123 and Inbred line NP 804 has PVP Certificate No. 8700151.

TABLE 2

Combined Location and Year Performance Data
(1993–1994; 50 environments; 90–100 RM Markets)

| Hybrid | YLD (bu/a) | MST % | STK (BR) % | RT % | HUS % | PLT HT % | Ear HT % |
|---|---|---|---|---|---|---|---|
| NP 991 X NP 904 | 158 | 21.3 | 3 | 1 | 1256 | 272 | 98 |
| NP 904 X NP 807 | 151 | 21.0 | 4 | 5 | 1204 | 261 | 99 |
| LSD | 5.0 | 0.6 | 1.0 | 2 | 15.0 | 11.0 | 6.0 |

NP 991 X NP 904 is distinguished from similar hybrids in that it has competitive yield, very strong roots, good stalk quality, good grain quality, easy shelling and fast drydown compared to similar hybrids in the same maturity zone.

As used herein the term plant includes plant cells, plant protoplasts, plant cell tissue cultures including that from which corn plants fertile or otherwise can be regenerated, plant calli and plant cell clumps, and differentiated forms of plants such as, but not limited to embryos, pollen, stamen, anthers, flowers, kernels, ears, cobs, leaves, stalks, roots, shoots, plantlets, silks and kernels.

Methods of cell and tissue culture and regeneration are well known in the art and described for example in "Plant Tissue Culture Manual: Fundamentals and Application", Ed. K. Lindsey, Kluwer (1991) and in Green and Rhodes, "Plant Regeneration in Tissue Culture of Maize", Maize for Biological Research (Plant Molecular Biology Association, Charlottesville, Va., 1982, pp. 367–372), which are hereby incorporated by reference.

As is well known corn can be put to a wide variety of uses not only as livestock feed but also for human consumption of corn kernels and as a raw material in industry. Both grain and non-grain portions of the plant are used as a livestock feed for swine, cattle and poultry. In the food industry corn is used in wet and dry milling. In wet milling there is the separation of the germ, hull gluten and starch. Germ is used to produce corn oil and germ cake for feed. Corn starch may be packaged for human consumption or used in food products such as sauces, gravies, puddings, sweeteners, syrups, and baking powder. Other nonedible uses include textiles, paper, adhesives, cosmetics, explosives, corn binders, laundry purposes and agricultural formulations. Dry milling is used to produce breakfast foods, grits, cornmeal and corn flour. Other uses of corn include fuel, in the form of fuel alcohol or ethanol; seed; alcoholic beverages and construction.

DEPOSIT INFORMATION

Deposit of at least 2500 seeds of inbred corn line NP 991 has been made unrestrictedly available to the public via the American Type Culture Collection (ATCC), Rockville, Md. 20852 USA. The deposit made on Nov. 12, 1997 and corresponds to ATCC Deposit No. 209451. The seeds were from stock maintained by Northrup King Co. since prior to filing this application or any parents thereof. The deposit of inbred corn line NP 991 will be maintained in the ATCC depository, which is a public depository, for a period of 30 years, or 5 years after the most recent request, or for the effective life of the patent, whichever, is longer, and will be replaced if it becomes nonviable during that period. Additionally, with respect to Plant Variety Protection Certificates received and applied for, Applicant does not waive any infringement of its rights granted under this patent or under the Plant Variety Protection Act (7 U.S.C. 2312 et seq.).

It is claimed:

1. An inbred corn line designated NP 991, the seeds of which have been deposited as ATCC Accession No. 209451.

2. A corn plant or the parts of inbred corn line designated NP 991 of claim 1.

3. An inbred corn plant having all physiological and morphological characteristics of the plant of claim 2.

4. Seeds of the inbred corn line NP 991 of claim 1.

5. A corn plant regenerated from the cells or protoplasts of a culture of corn tissue and a genotype capable of expressing all the physiological and morphological characteristics of the corn plant of claim 2, the seed of which has been deposited and having ATCC Accession No. 209451.

6. Hybrid corn seed produced by crossing plants of inbred corn line designated NP 991, the seed having ATCC Accession No. 209451 with plants of another inbred corn line having a genotype different from corn line NP 991.

7. Hybrid corn plants produced by growing the corn seed of claim 6.

8. A tissue culture of regenerable cells of the corn plant of claim 7.

9. Hybrid seed of claim 6 wherein the corn line NP 991 is the female parent.

10. Hybrid corn seeds produced by:
  a) planting in pollinating proximity seeds of inbred corn line NP 991 having ATCC Accession No. 209451 and a second inbred line having a genotype different from NP 991;
  b) cultivating corn plants resulting from said planting until time of flowering;
  c) emasculating said flowers of plants of one of the corn inbred lines;
  d) allowing cross pollination to occur between said inbreds, and
  e) harvesting the seeds produced on said plants of inbred line NP 991.

11. Hybrid corn plants grown from the hybrid corn seed produced according to claim 10.

* * * * *